US011116538B2

(12) United States Patent
Graham et al.

(10) Patent No.: US 11,116,538 B2
(45) Date of Patent: Sep. 14, 2021

(54) MEDICANT DELIVERY DEVICE

(71) Applicant: GYRUS ACMI, INC., Southborough, MA (US)

(72) Inventors: Madeline C. Graham, Redmond, WA (US); Hugo X. Gonzalez, Woodinville, WA (US)

(73) Assignee: GYRUS ACMI, INC., Southborough, MA (US)

(*) Notice: Subject to any disclaimer, the term of this patent is extended or adjusted under 35 U.S.C. 154(b) by 195 days.

(21) Appl. No.: 16/184,231

(22) Filed: Nov. 8, 2018

(65) Prior Publication Data
US 2020/0146705 A1    May 14, 2020

(51) Int. Cl.
| A61B 17/32 | (2006.01) |
| A61B 17/3205 | (2006.01) |
| A61B 1/267 | (2006.01) |

(52) U.S. Cl.
CPC ........ *A61B 17/3205* (2013.01); *A61B 1/2676* (2013.01); *A61B 17/320016* (2013.01)

(58) Field of Classification Search
CPC ............ A61B 17/3205; A61B 17/3207; A61B 17/320725; A61B 17/320783; A61B 17/34; A61B 17/320016; A61B 17/32002; A61B 2017/320791; A61B 2017/320056; A61B 17/32056; A61B 17/320758; A61B 17/3478; A61B 10/0233; A61B 2010/045; A61B 17/32; A61B 17/3209; A61F 9/00763

See application file for complete search history.

(56) References Cited

U.S. PATENT DOCUMENTS

| 2002/0058885 A1* | 5/2002 | Burbank | A61B 17/32056 600/567 |
| 2002/0077648 A1* | 6/2002 | Lee | A61B 17/320725 606/170 |
| 2008/0300594 A1* | 12/2008 | Goto | A61B 17/320725 606/46 |
| 2012/0130417 A1* | 5/2012 | Lepulu | A61M 25/0082 606/198 |
| 2016/0166243 A1* | 6/2016 | Wilson | A61B 17/3209 606/170 |
| 2017/0150984 A1* | 6/2017 | Breen | A61B 17/3211 |

* cited by examiner

*Primary Examiner* — Melanie R Tyson
(74) *Attorney, Agent, or Firm* — Clements Bernard Walker; Michael S. Smith (57) ABSTRACT

An example medical instrument for creating larger voids within target tissue. Medicants could be injected into these larger voids for diffusion into the surrounding tissue. An exemplary medical device includes a tissue penetrating device, a pocket creation device and a handle. The handle includes a first component connected to the tissue penetrating device and a second component connected to the pocket creation device. When the second component is at a first position relative to the first component, the pocket creation device is in a non-pocket creation configuration. When the second component is at a second position relative to the first component, the pocket creation device is in a pocket creation configuration, wherein the pocket creation device is slidably received within the tissue penetrating device and the handle.

7 Claims, 8 Drawing Sheets

MEDICANT DELIVERY DEVICE

BACKGROUND

There are several medical situations where it is desired to deliver substances by injection to a relatively large volume of tissue. If a substance is delivered by a single point injection, the problems that may arise are (a) the substance cannot spread throughout the volume in sufficient time; (b) too much dilution may occur during the spreading; (c) the distribution of the substance within the volume may be very inhomogeneous; and (d) unwanted spreading to regions away from the target volume may occur. One solution to this problem is to give smaller injections at several sites within the target volume. This approach has at least a few disadvantages: (a) multiple needle stab wounds are created; (b) accuracy of placement is limited; and (c) the time for the procedure may be increased.

SUMMARY

The present invention relates to an improved hypodermic needle and fluid injection device.

The present invention provides an example medical instrument for creating larger voids within target tissue. Medicants could be injected into these larger voids for diffusion into the surrounding tissue. An exemplary medical device includes a tissue penetrating device, a pocket creation device and a handle. The handle includes a first component connected to the tissue penetrating device and a second component connected to the pocket creation device. When the second component is at a first position relative to the first component, the pocket creation device is in a non-pocket creation configuration. When the second component is at a second position relative to the first component, the pocket creation device is in a pocket creation configuration, wherein the pocket creation device is slidably received within the tissue penetrating device and the handle.

In one aspect of the invention, the pocket creation device includes a stylet and a stylet handle component connected to a proximal end of the stylet. The stylet is received within a lumen of the tissue penetrating device. The pocket creation device further includes a stylet force device that maintains a longitudinal compression force on the stylet.

In another aspect of the invention, the tissue penetrating device includes a tissue piercing distal tip and one or more slots proximal from the tip. The one or more slots expose a lumen of the tissue penetrating device.

In still another aspect of the invention, the stylet includes one or more prongs configured to bend away from a longitudinal axis of the tissue penetrating device, when the stylet experiences the longitudinal compression force. When the one or more prongs bend away from the longitudinal axis at least a portion of the one or more prongs extends through a corresponding one of the slots.

In yet another aspect of the invention, the one or more prongs includes an edge configured to cut tissue upon motion about the longitudinal axis.

In still yet another aspect of the invention, the pocket creation device includes a clocking device configured to align the one or more prongs with the one or more slots.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 6-1 is an x-ray view of a distal end of an injection component formed in accordance with an embodiment of the present invention;

FIG. 6-2 is an x-ray view of the injection component of FIG. 6-1 in a different operational state;

FIG. 6-3 is a side view of a stylet device used in the injection component of FIGS. 6-1 and 6-2 having a first pattern of injection;

FIG. 6-4 is a side view of a stylet device used in the injection component of FIGS. 6-1 and 6-2 having a second pattern of injection;

FIG. 7-1 is an x-ray view of the injection component in a first operational state;

FIG. 7-2 is an x-ray view of the injection component of FIG. 7-1 in a second operational state;

FIG. 8-1 is an x-ray view of a distal end of an injection component formed in accordance with an embodiment of the present invention;

FIG. 8-2 is an x-ray view of the injection component of FIG. 8-1 in a first operational state;

FIG. 9-1 is a partial cross-sectional view of a distal end of an injection component formed in accordance with an embodiment of the present invention;

FIG. 9-2 is a partial cross-sectional view of the stylet component of FIG. 9-1 in a first operational state;

FIG. 11-1 is a side view of a distal end of an injection component formed in accordance with an embodiment of the present invention;

FIG. 11-2 is side view of a stylet of the injection component of FIG. 11-1; and

FIG. 11-3 is an x-ray view of a distal end of the injection component of FIG. 11-1.

DETAILED DESCRIPTION

The following description is merely exemplary in nature and is not intended to limit the present disclosure, application, or uses.

Figure 1:
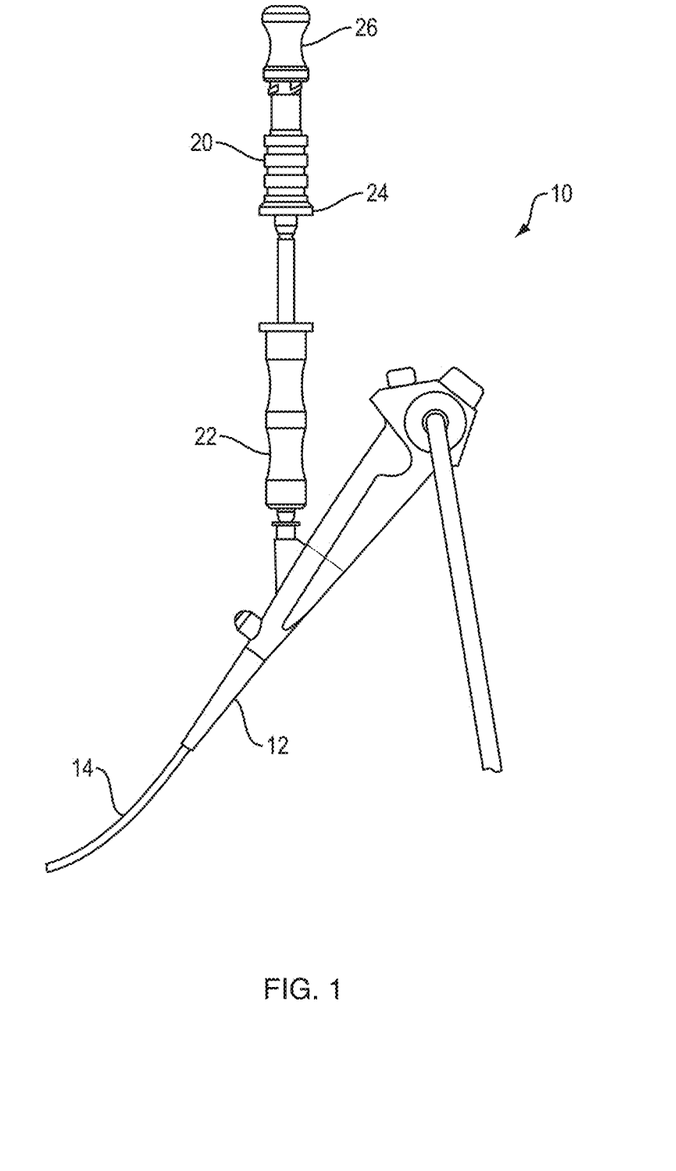
FIG. 1 is a side view of external components of an injection system formed in accordance with an embodiment of the present invention.

FIG. 1 shows an exemplary system 10 for injecting fluid or medicants into target tissue. The system 10 includes an injection device 20 that is received through a handle and an insertion tube 14 of an endoscope 12 (e.g., bronchoscope). The injection device 20 may or may not be used with a sheath. If the injection device 20 is used with the sheath (not shown), a handle of the injection device 20 includes a base component 22 connected to the sheath, an actuator component 24 connected to a needle device (not shown) slidably received within the sheath and a stylet handle component 26 connected to a stylet (not shown) slidably received within the needle device.

The actuator component 24 allows a user to extend a distal end of the needle distally from a distal end of the sheath. Force applied by the user to the actuator component 24 translates into a force at the distal end of the needle, thus allowing for penetration of the needle into target tissue (e.g., lesion or tumor).

A stylet extension mechanism (shown by example in FIG. 5) allows for extension of at least a portion of the stylet from a distal section of the needle. The stylet extension mechanism may include components located in the actuator component 24 and/or the stylet handle component 26. Examples of the stylet extension mechanism are shown and/or described below.

Figure 2:
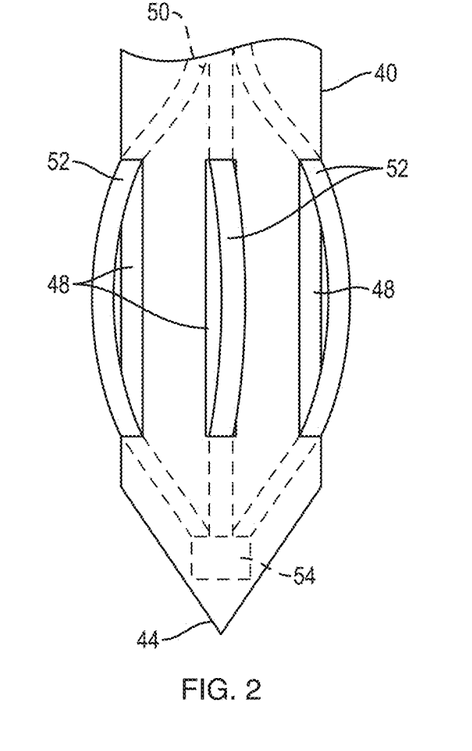
FIG. 2 is an x-ray view of a distal end of a component of the injection system of FIG. 1.

As shown in FIG. 2, a needle 40 of the injection device 20 (FIG. 1) includes a trocar or occluded tip 44. The needle 40 includes one or more slots 48 proximal from the tip 44. The slots 48 expose a lumen of the needle 40 to the exterior of the needle 40. A proximal end of a stylet 50 is connected to the stylet handle component 26. A distal end of the stylet 50 is split into multiple flexible prongs 52 at a distal section. The distal ends of the prongs 52 are connected to each other at a distal plug 54. The stylet 50 and the prongs 52 may be manufactured by laser cutting a hypotube or rod.

Figure 3:
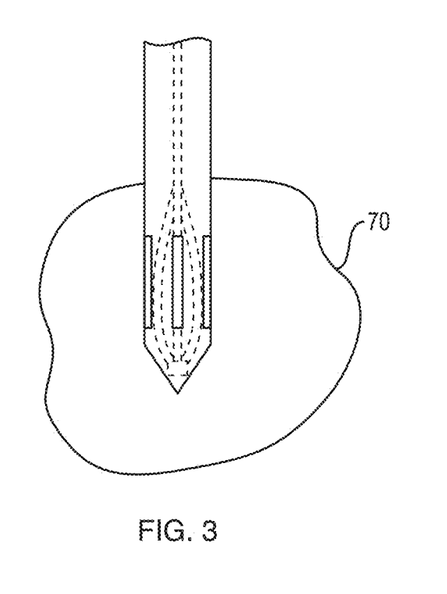
FIG. 3 is a side, x-ray view of the distal end of the component of FIG. 2 in a first configuration.
Figure 4:
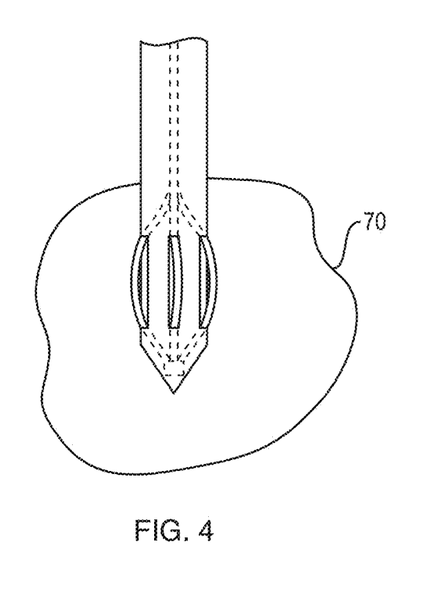
FIG. 4 is a side x-ray view of the distal end of the component of FIG. 2 in a second configuration.

Once the needle 40 has been positioned adjacent to previously identified target tissue with the help of the endoscope 12, the actuator component 24 is advanced distally causing the needle 40 to penetrate the target tissue 70 (FIG. 3). Next, the user applies a distal force to the stylet handle component 26. When pressure/force is applied to the stylet handle component 26, the distal plug 54 makes contact with the distal end of the lumen of the needle 40 or inside of the tip 44. This causes the prongs 52 of the stylet 50 bend outward from a longitudinal axis of the needle 40, thus passing through the slots 48. The prongs 52 protruding from the slots 48 penetrate or apply pressure to the surrounding target tissue 70 (FIG. 4). Then the needle 40, if desired, could be rotated, allowing the prongs 52 to cut the tissue and subsequently create more or larger pockets within the target tissue for fluid, such as a medicant, to flow. Once the distal force is released, the prongs 52 retract within the needle 40 and return to the predeployed position. Then fluid could be injected through the needle lumen and out of the slots 48 at the tip of the needle 40. The stylet 52 would be thin enough that there would be room within the needle lumen for fluid to flow.

In one embodiment, the prongs 52 have edges sharp enough to cut tissue. Thus, when the needle 40 is rotated, the sharp edges of any protruding prongs 52 will cut surrounding tissue.

In one embodiment, the distal plug 54 and the tip 44 are configured such that when the distal plug 54 is forced against the interior of the tip 44, the distal plug 54 rotates into proper alignment so that the prongs 52 rotate to align with the slots 48. This is considered a clocking mechanism. Other clocking mechanisms can be used.

Figure 5:
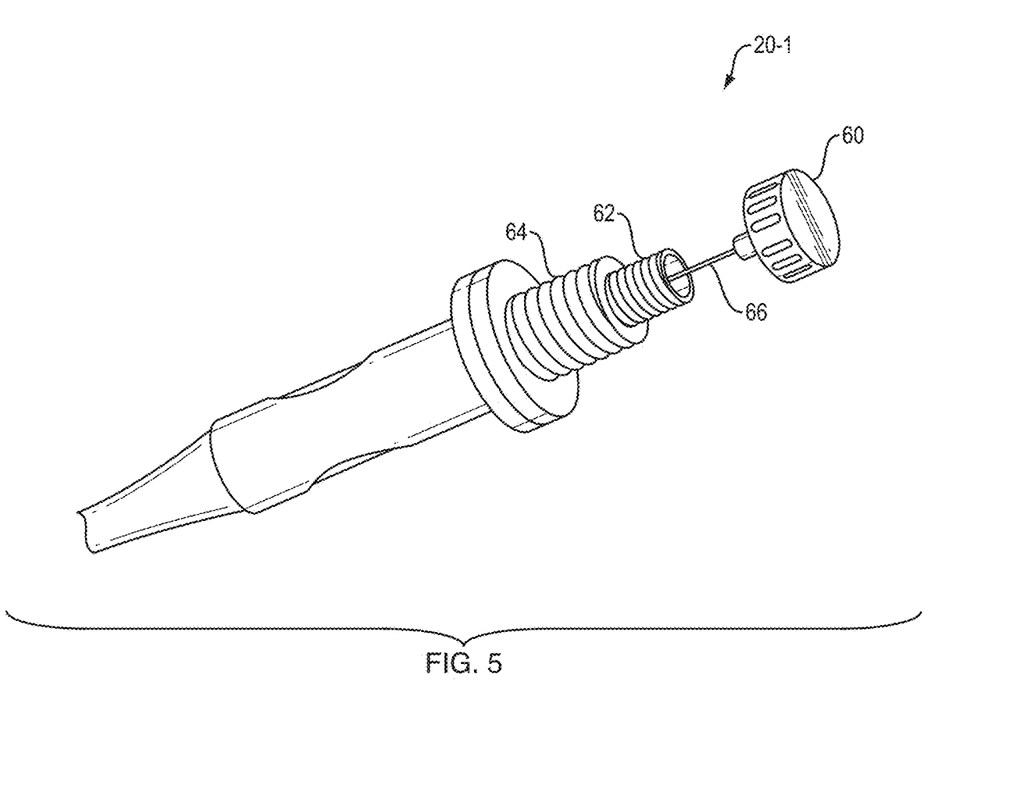
FIG. 5 is a perspective view of a handle associated with the component of FIG. 2.
Figure 10:
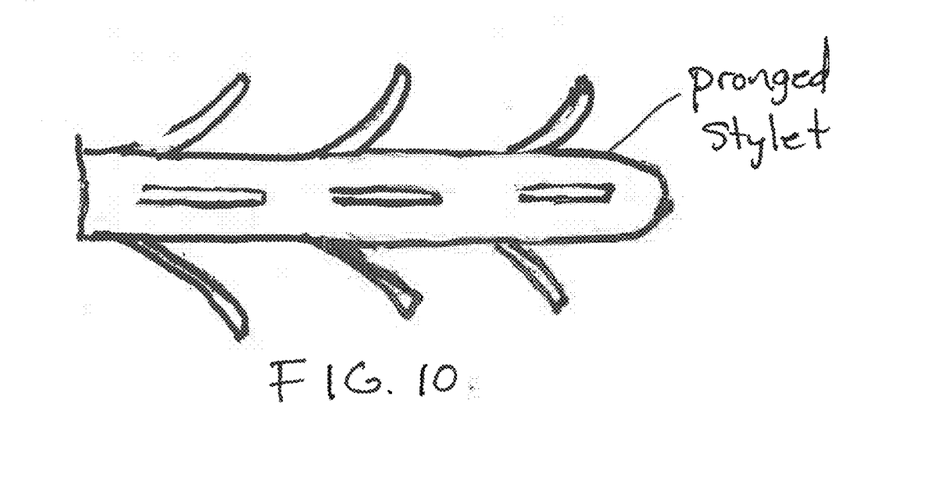
FIG. 10 is a side view of stylet device formed in accordance with an embodiment of the present invention.
Figure 61:
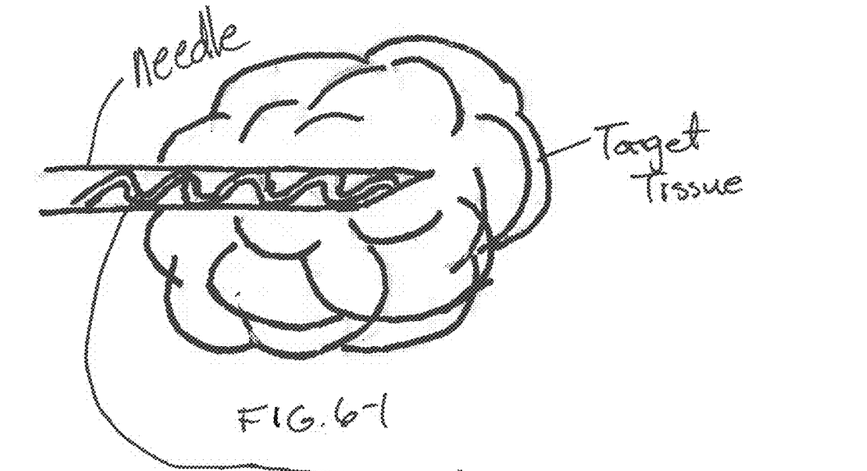
Figure 62:
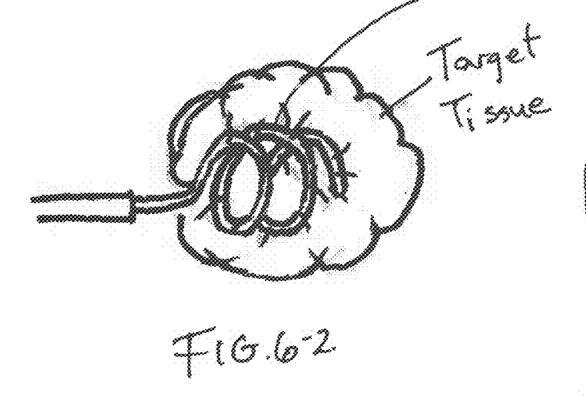
Figure 63:
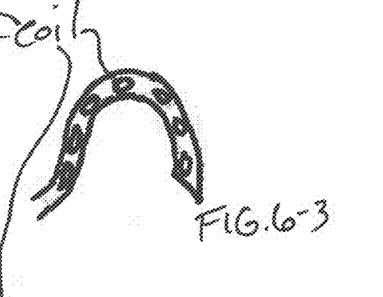
Figure 64:
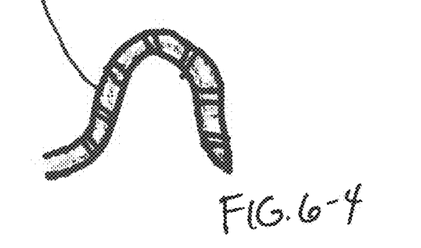
Figures 71, 72:
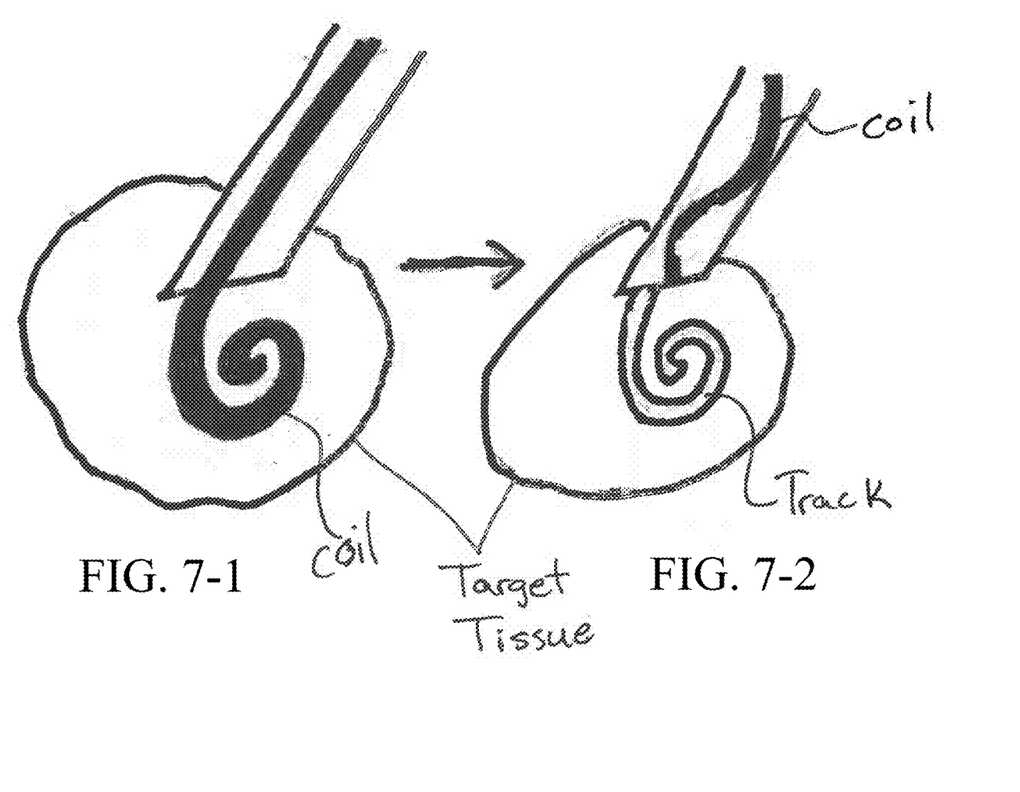
Figure 81:
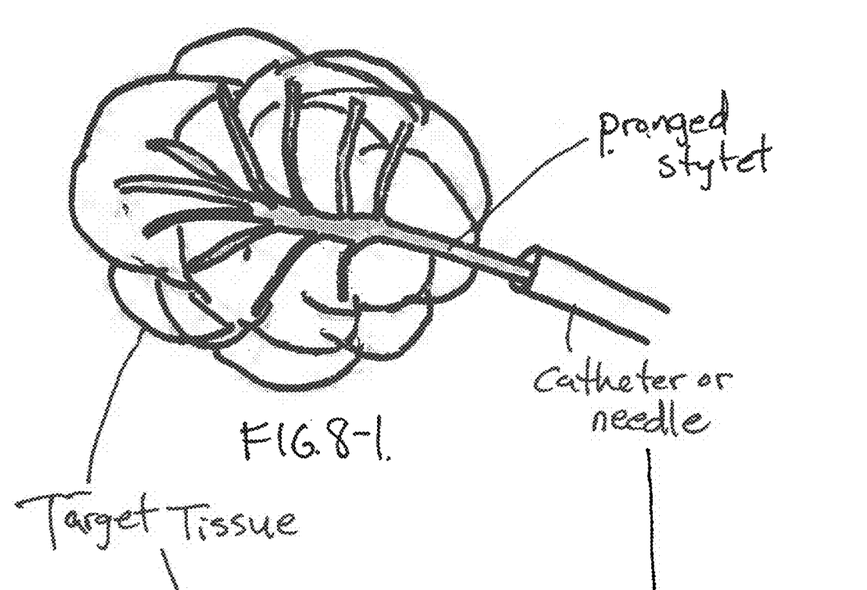
Figure 82:
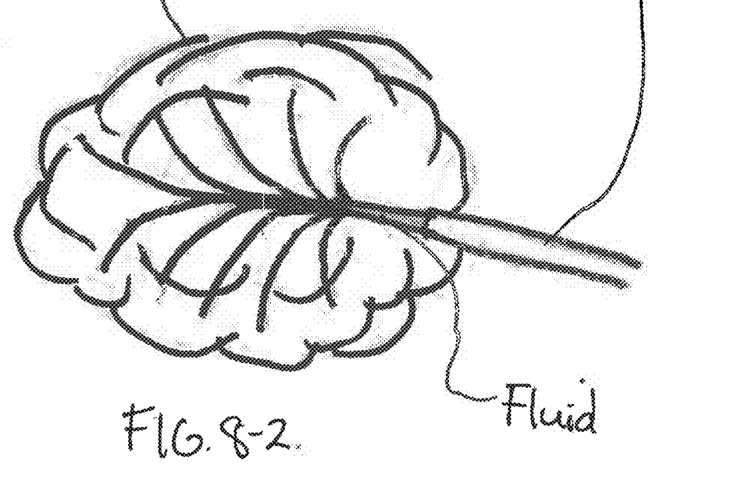
Figure 91:
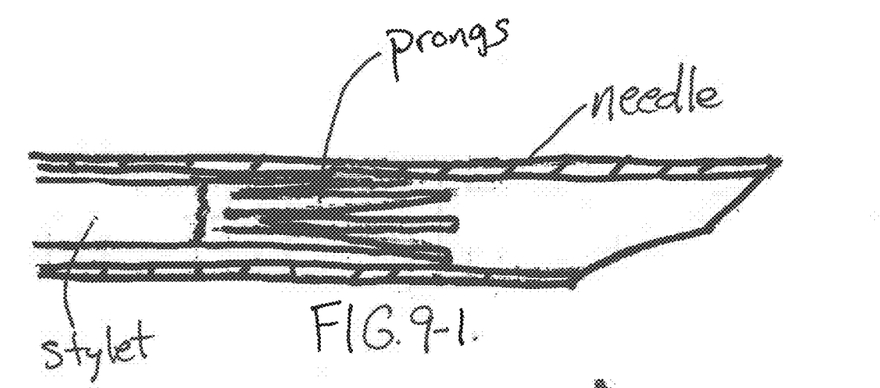
Figure 92:
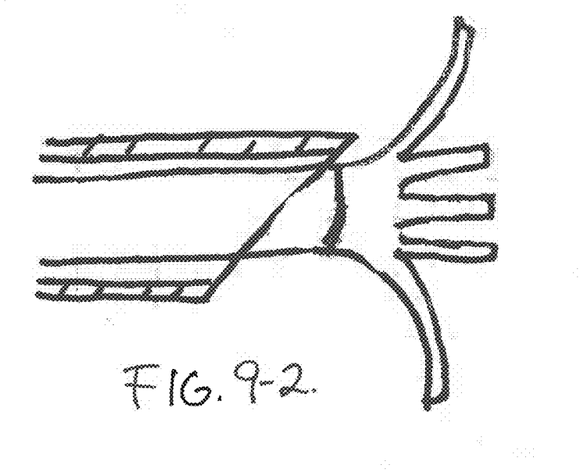
Figure 111:
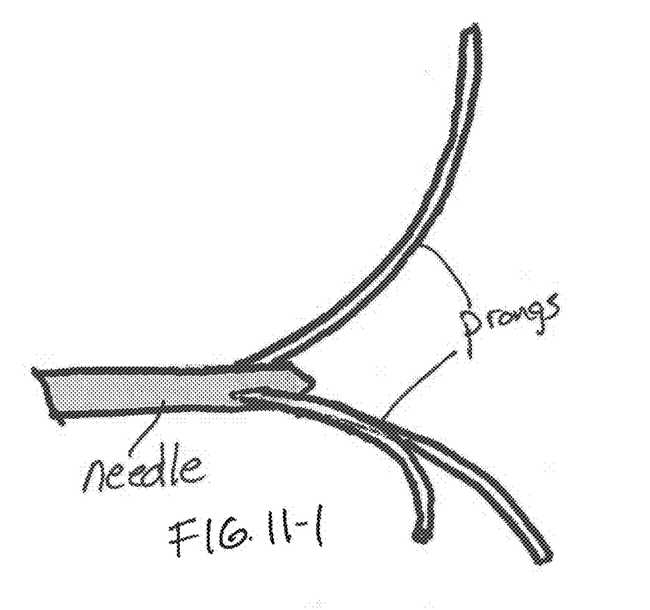
Figure 112:
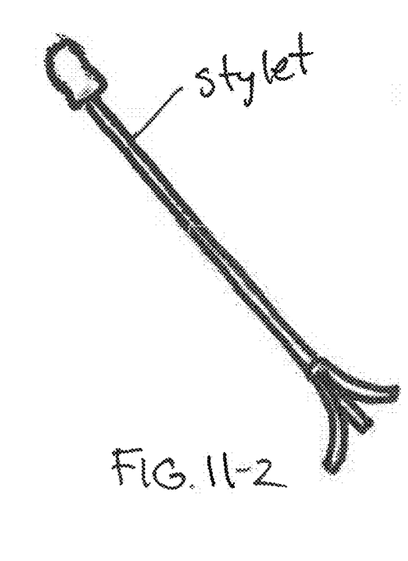
Figure 113:
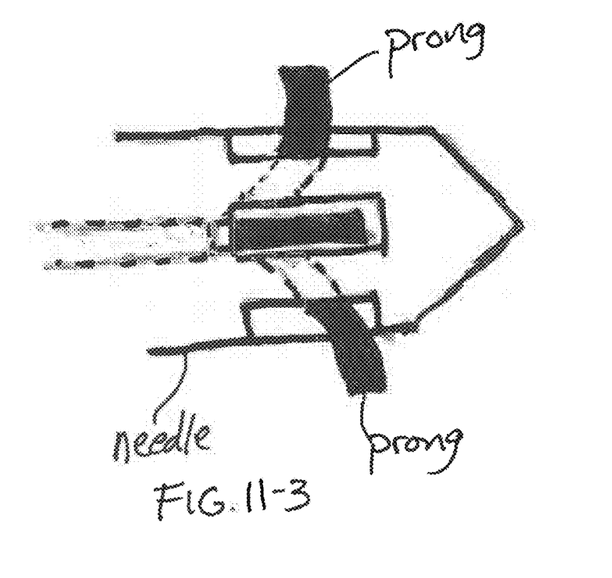

In one embodiment, as shown in FIG. 5, a stylet handle component 20-1 includes a screw/twist knob 60 that mates to a luer 62 at the proximal end of an actuator handle component 64. If the stylet twist knob 60 is not connected to the luer 62, but simply rests on top of it, then a distal end of a stylet 66 will sit in the middle of a bevel cut of the distal end of a needle. The prongs 52 will not be forced to expand out of the needle slots 48. By connecting the stylet knob 60 and luer 62, the stylet 66 compresses against the tip 44 of the needle, thus causing the prongs 52 to protrude through the slots 48. How far the prongs 52 protrude depends on how far the knob 60 is twisted onto the luer 62.

In one embodiment, a stylet knob includes a counterbore with a spring. When the knob rests on the luer at the proximal end of the device, a distal tip of the stylet attached to the knob lies within the distal end of the needle. When the spring is compressed by a distal force applied by a user to the stylet knob, the distal force causes the prongs of the stylet to extend out of slots at the distal end of the needle.

Embodiments

A. A medical device comprising: a tissue penetrating device; a pocket creation device; and a handle comprising: a first component connected to the tissue penetrating device; and a second component connected to the pocket creation device, wherein when the second component is at a first position relative to the first component, the pocket creation device is in a non-pocket creation configuration, wherein when the second component is at a second position relative to the first component, the pocket creation device is in a pocket creation configuration, wherein the pocket creation device is slidably received within the tissue penetrating device and the handle.

B. The medical device of A, wherein the pocket creation device comprises: a stylet; and a stylet handle component connected to a proximal end of the stylet, wherein the stylet is received within a lumen of the tissue penetrating device.

C. The medical device of A, wherein the pocket creation device further comprises a stylet force device configured to maintain a longitudinal compression force on the stylet.

D. The medical device of B or C, wherein the tissue penetrating device comprises: a tissue piercing distal tip; and one or more slots proximal from the tip, the one or more slots configured to expose a lumen of the tissue penetrating device.

E. The medical device of D, wherein the stylet comprises one or more prongs configured to bend away from a longitudinal axis of the tissue penetrating device when the stylet experiences the longitudinal compression force, wherein when the one or more prongs bend away from the longitudinal axis at least a portion of the one or more prongs extends through a corresponding one of the slots.

F. The medical device of E, wherein the one or more prongs comprise an edge configured to cut tissue upon motion about the longitudinal axis.

G. The medical device of E or F, wherein the pocket creation device comprises a clocking device configured to align the one or more prongs with the one or more slots.

H. A system comprising: a medical imaging device comprising: a handle; an insertion tube coupled to the handle; and an imaging component comprising a transducer located at a distal end of the insertion tube, the imaging component configured to generate an image of tissue near the distal end of the insertion tube; and a medical device comprising: a tissue penetrating device slidably received in the handle and the insertion tube of the medical imaging device, the tissue penetrating device configured to penetrate tissue within a field of view of the transducer; a pocket creation device; and a handle comprising: a first component connected to the tissue penetrating device; and a second component connected to the pocket creation device, wherein when the second component is at a first position relative to the first component, the pocket creation device is in a non-pocket creation configuration, wherein when the second component is at a second position relative to the first component, the pocket creation device is in a pocket creation configuration, wherein the pocket creation device is slidably received within the tissue penetrating device and the handle.

I. The system of H, wherein the pocket creation device comprises: a stylet; and a stylet handle component connected to a proximal end of the stylet, wherein the stylet is received within a lumen of the tissue penetrating device.

J. The system of I, wherein the pocket creation device further comprises a stylet force device configured to maintain a longitudinal compression force on the stylet.

K. The system of I or J, wherein the tissue penetrating device comprises: a tissue piercing distal tip; and one or more slots proximal from the tip, the one or more slots configured to expose a lumen of the tissue penetrating device.

L. The system of K, wherein the stylet comprises one or more prongs configured to bend away from a longitudinal axis of the tissue penetrating device when the stylet experiences the longitudinal compression force, wherein when the one or more prongs bend away from the longitudinal axis at least a portion of the one or more prongs extends through a corresponding one of the slots.

M. The system of K, wherein the one or more prongs comprises an edge configured to cut tissue upon motion about the longitudinal axis.

N. The system of L or M, wherein the pocket creation device comprises a clocking device configured to align the one or more prongs with the one or more slots.

The description of the invention is merely exemplary in nature and variations that do not depart from the gist of the invention are intended to be within the scope of the invention. Such variations are not to be regarded as a departure from the spirit and scope of the invention.

What is claimed is:

1. A medical device comprising:
    a handle;
    a tissue penetrating device couplable at a proximal end to a distal end of the handle; and
    a pocket creation device couplable at a proximal end to the distal end of the handle, the pocket creation device configured to be slidably received within the tissue penetrating device, a distal end of the pocket creation device comprises one or more prongs having an edge configured to cut tissue upon motion about a longitudinal axis,
    wherein the one or more prongs are configured to be disposed within a lumen of the tissue penetrating device in response to the medical device being in a non-pocket creation configuration,
    wherein the one or more prongs are configured to protrude from the tissue penetrating device in response to the medical device being in a pocket creation configuration,
    wherein the pocket creation device is slidably received within the tissue penetrating device,
    wherein the pocket creation device comprises a clocking mechanism configured to align the one or more prongs with the one or more slots.

2. The medical device of claim 1, wherein the proximal end of the pocket creation device comprises:
    a stylet; and
    a stylet handle component connected to a proximal end of the stylet,
    wherein the stylet is received within lumens of the handle and the tissue penetrating device.

3. The medical device of claim 2, wherein the handle further comprises a stylet securing device configured to receive the stylet handle in a plurality of longitudinal positions relative to the handle, thus compressing a distal end of the stylet against a distal end of the tissue penetrating device.

4. The medical device of claim 2, wherein the tissue penetrating device comprises:
    a tissue piercing distal tip; and
    one or more slots proximal from the tip, the one or more slots configured to expose the lumen of the tissue penetrating device.

5. The medical device of claim 4, wherein the one or more prongs are configured to bend away from the longitudinal axis of the tissue penetrating device and protrude out of the one or more slots in response to the stylet experiencing a longitudinal compression force.

6. A system comprising:
    a medical imaging device comprising:
        a handle;
        an insertion tube coupled to the handle; and
        an imaging component configured to generate an image of tissue near the distal end of the insertion tube; and
    a medical device comprising:
        a handle comprising a stylet securing device;
        a tissue penetrating device slidably received in the handle of the medical imaging device and the insertion tube of the medical imaging device, the tissue penetrating device configured to penetrate tissue within a field of view of the imaging component, the tissue penetrating device comprises:
            a tissue piercing distal tip; and
            one or more slots proximal from the tip, the one or more slots configured to expose a lumen of the tissue penetrating device; and
        a pocket creation device comprising:
            a stylet receivable within a lumen of the tissue penetrating device, the stylet comprises one or more prongs having an edge configured to cut tissue upon motion about a longitudinal axis; and
            a stylet handle connected to a proximal end of the stylet, the stylet handle configured to be receivable by the stylet securing device in a plurality of longitudinal positions relative to the handle of the medical device and thus maintain a longitudinal compression force on the stylet against a distal end of the tissue penetrating device,
        wherein the one or more prongs being configured to bend away from a longitudinal axis of the tissue penetrating device when the stylet experiences the longitudinal compression force,
        wherein in response to the one or more prongs bending away from the longitudinal axis, at least a portion of the one or more prongs configured to extend through a corresponding one of the slots.

7. The system of claim 6, wherein the pocket creation device comprises a clocking device configured to align the one or more prongs with the one or more slots.

* * * * *